United States Patent
Park et al.

(10) Patent No.: US 11,452,705 B2
(45) Date of Patent: Sep. 27, 2022

(54) ORAL DRUG DELIVERY COMPOSITION CONTAINING OXALIPLATIN AND METHOD FOR PREPARING SAME

(71) Applicant: ICURE BNP CO., LTD., Uiwang-si (KR)

(72) Inventors: Jin Woo Park, Seoul (KR); Young Ro Byun, Seoul (KR); Young Kweon Choi, Seoul (KR); Kwan Young Chang, Seoul (KR); Jae Bum Lee, Seoul (KR)

(73) Assignee: ICURE BNP CO., LTD., Uiwang-si (KR)

( * ) Notice: Subject to any disclaimer, the term of this patent is extended or adjusted under 35 U.S.C. 154(b) by 170 days.

(21) Appl. No.: 16/621,942

(22) PCT Filed: Nov. 30, 2017

(86) PCT No.: PCT/KR2017/013958
§ 371 (c)(1),
(2) Date: Dec. 12, 2019

(87) PCT Pub. No.: WO2018/230788
PCT Pub. Date: Dec. 20, 2018

(65) Prior Publication Data
US 2021/0290586 A1    Sep. 23, 2021

(30) Foreign Application Priority Data
Jun. 12, 2017   (KR) ........................ 10-2017-0073215

(51) Int. Cl.
| | |
|---|---|
| *A61K 31/282* | (2006.01) |
| *A61K 47/54* | (2017.01) |
| *A61K 9/00* | (2006.01) |
| *A61K 9/107* | (2006.01) |
| *A61K 9/113* | (2006.01) |
| *A61K 31/12* | (2006.01) |
| *A61K 31/353* | (2006.01) |
| *A61K 31/513* | (2006.01) |
| *A61K 31/519* | (2006.01) |

(52) U.S. Cl.
CPC .......... *A61K 31/282* (2013.01); *A61K 9/0056* (2013.01); *A61K 9/1075* (2013.01); *A61K 9/113* (2013.01); *A61K 31/12* (2013.01); *A61K 31/353* (2013.01); *A61K 31/513* (2013.01); *A61K 31/519* (2013.01); *A61K 47/554* (2017.08)

(58) Field of Classification Search
CPC .. A61K 31/282; A61K 47/554; A61K 9/0056; A61K 9/1075; A61K 9/113; A61K 31/12; A61K 31/353; A61K 31/513; A61K 31/519
See application file for complete search history.

(56) References Cited

U.S. PATENT DOCUMENTS

2013/0281916 A1    10/2013   Wagstaffe et al.

FOREIGN PATENT DOCUMENTS

| JP | 2014-504276 A | 2/2014 |
|---|---|---|
| KR | 10-2015-010472 A | 9/2015 |

OTHER PUBLICATIONS

Pangeni et al., "Multiple nanoemulsion system for an oral combinational delivery of oxaliplatin and 5-fluorouracil preparation and in vivo evaluation", International Journal of Nanomedicine, 2016, vol. 11, p. 6379-6399.
Jeon et al., "Preparation of Oxaliplatin-Deoxycholic Acid Derivative Nanocomplexes and In Vivo Evaluation of Their Oral Absorption and Tumor Growth Suppression", Journal of Nanoscience and Nanotechnology, 2016, vol. 16, p. 2061-2064.
EESR dated Mar. 20, 2021, 6 pages, for corresponding application EP 17913783.1.

*Primary Examiner* — James D. Anderson
*Assistant Examiner* — William Y Lee
(74) *Attorney, Agent, or Firm* — Vorys, Sater, Seymour and Pease LLP; Mih Suhn Koh (57) ABSTRACT

Provided are an oral delivery composition including oxaliplatin, a water-soluble anticancer agent, and a preparation method thereof, including forming an ionic complex with a bile acid derivative, which is an oral absorption promoter, and oxaliplatin, and incorporating it into the inner aqueous phase of a water-in-oil-in-water (w/o/w) multiple nanoemulsions, thereby obtaining the oral delivery composition with improved oral bioavailability of oxaliplatin, a water-soluble anticancer agent, avoiding the inconvenience and problems of injection, improving patient compliance, and reducing medical costs.

14 Claims, 9 Drawing Sheets

ORAL DRUG DELIVERY COMPOSITION CONTAINING OXALIPLATIN AND METHOD FOR PREPARING SAME

STATEMENT REGARDING GOVERNMENT RIGHTS

The present invention was undertaken with the support of the Korea Institute for Advancement of Technology No. HI13C3228 (Project Name: Development of a platform technology for oral anti-cancer dosage form, Industrial Technology Classification: Pharmaceutical preparation), funded by the Ministry Trade, Industry and Energy.

BACKGROUND

Technical Field

The present invention relates to an oral delivery composition comprising a complex by ion-pairing of an oxaliplatin as a water-soluble active substance and a bile acid derivative as an oral absorption enhancer in an internal aqueous phase of a multiple water-in-oil-in-water (w/o/w) nanoemulsion, and a method for preparing the same.

Background Art

Oxaliplatin (cis-[(1R,2R)-1,2-cyclohexanediamine-N,N'][oxalato(2-)-O,O']platinum, OXA) is composed of platinum (Pt) and 1,2-diaminocyclohexane, and is a compound having an oxalate ligand as a leaving group, and is a third generation platinum antitumor compound which exerts its effects by interfering with DNA replication and transcription machinery through nuclear DNA adduct formation. These Pt-DNA adducts typically take the form of Pt-guanine-guanine bonds. At the nucleotide level, Pt-DNA complexes will either activate DNA repair mechanisms or apoptotic pathways.

Oxaliplatin is also marketed for the treatment of advanced colorectal cancer and metastatic gastric cancer under the trade name Eloxatin®, and may also be administered in combination with 5-fluorouracil (5-FU) and leucovorin. In particular, metastatic colorectal cancer uses chemotherapy, such as Eloxatin® (oxaliplatin) or FOLFOX (in combination with fluorouracil/leucovorin/oxaliplatin), FOLFIRI (in combination with fluorouracil/leucovorin/irinotecan), and Avastin (Avastin®, bevacizumab) from Genentech/Roche was approved by the US FDA in 2004.

Oxaliplatin is currently administered to patients only as an injection and should be diluted with water for injection, glucose solution or 0.9% sodium chloride solution immediately prior to administration to the patient in the form of a lyophilized formulation. However, the lyophilization process is complex and expensive to manufacture and also, reconstitution is necessary to use lyophilized products. However, in the reconstitution process, problems such as loss of oxaliplatin, generation of precipitate, generation of undesirable particles during reconstitution, and risk of exposure to contamination may occur, and in particular pollution is very serious because of the toxicity of antitumor substances.

Recently, oral chemotherapy is attracting increasing attention because it avoids the discomfort of injections after hospitalization and can be conducted at home, which can improve patient cooperation and quality of life.

In addition, a prolonged exposure of anti-cancer drugs to cancerous cells can be implemented by maintaining an appropriate plasma drug concentration, which can increase drug efficacy and decrease adverse effects, as well as facilitate the use of anti-cancer drugs for chronic treatment regimens as prophylactics against recurrence and metastasis.

However, oral delivery of anti-cancer drugs has many barriers due to physicochemical properties and physiological disorders of active ingredients.

Such barriers include pre-systemic metabolism, gastrointestinal (GI) instability, low aqueous solubility, poor intestinal membrane permeability, and high levels of P-glycoprotein (P-gp) efflux.

In particular, oxaliplatin exhibits poor oral bioavailability due to low intestinal membrane permeability, thus limiting the use of oral preparations. At present, attempts to make oxaliplatin into oral preparations are not well known, but oral formulations for effective local delivery of OXA to treat colorectal cancer tissue have been developed by encapsulation of OXA in pH-sensitive, mucoadhesive chitosan-based alginate microspheres and hyaluronic acid-coupled chitosan nanoparticles, followed by coating with Eudragit 5100, and 5-fluorouracil for local delivery of large intestine has been suggested by preparation in the form of pellets coated with pectin and ethyl cellulose and an oral preparation in the form of PLGA (poly(lactic-co-glycolic acid) nanoparticles.

Therefore, the present inventors have studied to prepare a water-soluble active substance such as oxaliplatin in the formulation for oral administration, and have formed a complex of oxaliplatin by ion-pairing with a bile acid derivative which is an oral absorption enhancer, and have completed the present invention by discovering that including it in the inner aqueous phase of multiple w/o/w (water-in-oil-water) nanoemulsions can increase the intestinal membrane permeability of the drug to make it into a formulation for oral administration.

(Reference 1) Journal of Nanoscience and Nanotechnology, 2016, Vol. 16, pp. 2061-2064.

DETAILED DESCRIPTION OF THE INVENTION

Summary

An object of the present invention is to prepare as a formulation for oral administration by increasing the intestinal membrane permeability of the drug by incorporating the oxaliplatin, a water-soluble anticancer agent, into the inner aqueous phase of the multiple w/o/w (water-in-oil-in-water) nanoemulsion, and to provide an oral delivery composition containing oxaliplatin and a method for preparing the same, which may improve the inconvenience and problems of the injection and contribute to improving patient compliance and reducing medical costs.

Technical Solution

The present invention provides a method for preparing an oral drug delivery composition comprising an oxaliplatin, including (a) step of adding a positively charged bile acid derivative to oxaliplatin to form an ionic (ion-pairing) complex;

(b) step of adding a mixture of primary surfactant and primary co-surfactant to the primary oil phase;

(c) step of preparing a water-in-oil (w/o) primary nanoemulsion by mixing the ionic complex with the mixture of step (b);

(d) step of manufacturing a w/o/w (water-in-oil-in-water) secondary nanoemulsion was prepared by adding a mixture of a secondary surfactant and a secondary co-surfactant to the w/o primary nanoemulsion;

The bile acid derivative is Na-deoxycholyl-L-lysyl-methylester (DCK), and comprises 0.5 to 5 moles per mole of oxaliplatin.

The oil phase in the w/o primary nanoemulsion is any one or more selected from the group consisting of silicone oil, ester oil, hydrocarbon oil, propylene glycol monocaprylate (Capryol 90), propylene glycol dicaprylocaprate/dicaprate (Labrafac PG), oleoyl polyoxyl-6 glycerides (Labrafil M1944 CS), lauroyl polyoxyl-6 glycerides (Labrafil M2130 CS), linoleoyl polyoxyl-6 glycerides (Labrafil M2125 CS), medium chain triglycerides (Labrafac), oleic acid, stearic acid, glyceryl dibehenate (Compritol 888), glycerol monostearate, and castor oil.

The oil phase in the w/o/w secondary nanoemulsion is comprises 1 to 40% by weight based on the total weight of the composition.

The primary and secondary surfactants are each independently one or more selected from the group consisting of poloxamer, caprylocapryl polyoxyl-8 glycerides (Labrasol), Cremophor, caprylic/capric mono- and diglycerides (Capmul MCM), lauroyl macrogol-32 glycerides (Gelucire 44/14), Solutrol, polysorbate (Tween), and sorbitan monolaurate (Span).

The primary and secondary surfactants are each independently one or more selected from the group consisting of diethylene glycol monoethyl ether (Transcutol HP), polysorbate, polyethylene glycol, butylene glycol, propylene glycol, ethanol, and isopropanol.

The mixture of the primary surfactant and the primary co-surfactant and the mixture of the secondary surfactant and the secondary co-surfactant are 5 to 90% by weight, based on the total weight of the composition.

The primary and secondary co-surfactants are mixed each independently in a weight ratio of 1:0.1 to 1:10 with respect to the primary and secondary surfactants.

In step (a) may further comprise an anti-aggregation agent selected from monosaccharides, polysaccharides, dietary fibers, gums, surfactants or proteins, wherein the anti-aggregation agent is comprised 0.1 to 100 parts by weight, based on 1 part by weight of oxaliplatin.

The w/o primary nanoemulsion further comprises a hydrophilic active ingredient selected from 5-fluorouracil (5-FU) or leucovorin in the inner aqueous phase.

In step (d), the w/o/w secondary nanoemulsion further comprises an oil-soluble active ingredient in oil phase selected from an insoluble anticancer agent, curcumin, quercetin, natural extract containing curcumin or quercetin as an active ingredient and a mixture thereof.

The present invention also provides an oral delivery composition comprising oxaliplatin prepared according to the above method.

Effects of the Invention

Oral delivery composition comprising oxaliplatin according to the present invention forms an ionic complex by combining oxaliplatin, a water-soluble anticancer agent with a bile acid derivative, an oral absorption enhancer, wherein the ionic complex is loaded in multiple w/o/w nanoemulsion to improve oral bioavailability, and can be prepared in a dosage form that can be orally administered. This improves the inconvenience and problems of using conventional injections, improves patient compliance, and contributes to the reduction of medical costs.

DETAILED DESCRIPTION

Hereinafter, an oral delivery composition comprising an oxaliplatin according to the present invention and a preparation method thereof will be described in detail.

Method for preparing an oral delivery composition comprising an oxaliplatin according to the present invention comprises (a) a step of forming an ionic complex by adding a positively charged bile acid derivative to oxaliplatin; (b) a step of adding a mixture of primary surfactant and primary co-surfactant to the primary oil phase; (c) a step of mixing the ionic complex with the mixture of step (b) to prepare a water-in-oil (w/o) primary nanoemulsion; (d) a step of preparing a water-in-oil-in-water (w/o/w) secondary nanoemulsion by adding a mixture of a secondary surfactant and a secondary co-surfactant to the w/o primary nanoemulsion;

The oxaliplatin is a hydrophilic and negatively charged active material, and a bile acid derivative, which is a positively charged oral absorption enhancer, is added to an aqueous solution of oxaliplatin to form a complex by ion-pairing.

The bile acid derivative is an amphiphilic material having a positive charge in an aqueous solution, and is preferably $N^{\alpha}$-deoxycholyl-L-lysyl-methylester (DCK) chemically bonded to L-lysine and deoxycholic acid. Also, it is preferably included in 0.5 to 5 moles, more preferably 1 to 2 moles per mole of oxaliplatin.

The DCK acts as an oral absorption enhancer, and is positively charged in an aqueous solution, thereby forming a complex by ion-pairing with a negatively charged hydrophilic active ingredient, and therefore can improve the lipophilic of the hydrophilic drug molecule to improve the distribution to the oil phase. Deoxycholic acid is an amphiphilic molecule consisting of a hydrophobic a portion and a hydrophilic p portion, which binds perpendicularly to the membrane surface of the cellular lipid bilayer and disturbs the acyl chains of the lipid matrix, so that it can improve the membrane permeability of the drug by increasing the flexibility of the intestinal cell membrane and the solubility of the fat-soluble drug in the membrane. Deoxycholic acid, a bile acid derivative combined with drugs, can also be recognized by the bile acid reuptake transporter present on the surface of the intestinal membrane, which leads to a high concentration gradient of the drug on the intestinal mucosa surface, increasing the passive diffusion of the drug into the intestinal mucosa. Therefore, the effect of enhancing absorption by the selective interaction of the ionic complex of the drug and the absorption enhancer with the bile acid resorption carrier, unlike conventional absorption enhancers, which are simply added by physical mixing, can increase the gastrointestinal absorption rate of hydrophilic drugs with minimal use because the absorption enhancer in the gastrointestinal tract after administration can be minimized by dilution by the fluid present in the gastrointestinal tract.

In order to manufacture the ion-pairing (or ionic) complex formed in the aqueous state in the form of a solid powder may be subjected to additional drying process, such as hot air drying, freeze drying, spray drying, and also an anti-aggregating agent may be added during the preparation of the ion-pairing complex for rapid redispersion in an aqueous solution of the ion-pairing complex in the form of a dry powder.

The anti-aggregating agent may be selected from monosaccharides, polysaccharides, dietary fibers, gums, surfactants or proteins, preferably mannitol, sucrose, lactose, glucose, trehalose, glycerol, fructose, maltose, dextran, cyclodextrin, glycine, poloxamer, polyvinylpyrrolidone, alanine or lysine, more preferably, it may be selected from poloxamer, polyvinylpyrrolidone, cyclodextrin, lactose or mannitol.

Moreover, the anti-aggregating agent may be included in an amount of 0.1 to 100 parts by weight, and more preferably 0.1 to 10 parts by weight, based on 1 part by weight of oxaliplatin.

The w/o primary nanoemulsion may further include a hydrophilic active ingredient that can exhibit an anticancer synergistic effect by co-administration with an ionic complex in the inner aqueous phase, wherein the hydrophilic active ingredient may be selected from 5-fluorouracil (5-FU) or leucovorin. By incorporating the hydrophilic active ingredient into the nanoemulsion formulation, the gastrointestinal absorption rate of the drug may be enhanced to improve oral bioavailability.

The primary oil phase used in the preparation of the w/o primary nanoemulsion is preferably any one or at least one selected from the group consisting of silicone oil, ester oils, hydrocarbon oils, propylene glycol monocaprylate (Capryol 90), propylene glycol dicaprolate/dicaprate (Labrafac PG), oleoyl polyoxyl-6 glycerides (Labrafil M1944 CS), lauroyl polyoxyl-6 glycerides (Labrafil M2130 CS), linoleoyl polyoxyl-6 glycerides (Labrafil M2125 CS), medium chain triglycerides (Labrafac), oleic acid, stearic acid, glyceryl dibehenate (Compritol 888), glycerol monostearate and castor oil.

The w/o primary nanoemulsion (oil phase) in the w/o/w secondary nanoemulsion is preferably included in an amount of 1 to 40% by weight, based on the total weight of the composition, more preferably in 10 to 30% by weight. When the content of the w/o primary nanoemulsion (oil phase) is less than 1% by weight, the drug may not be dissolved in the internal aqueous phase. If it exceeds 30% by weight, the particles of the nanoemulsion may become large, resulting in poor emulsion stability. In this case, the content of the w/o primary nanoemulsion (oil phase) does not include an emulsion stabilizer and means the total amount of w/o primary nanoemulsion (oil phase) in the total weight of the w/o/w secondary nanoemulsion including the secondary external aqueous phase.

In step (d), the w/o/w secondary nanoemulsion may further include a fat-soluble active ingredient capable of improving the pharmacological therapeutic efficacy of the ionic complex in the oil phase, wherein the fat-soluble active ingredient may be a poorly soluble anticancer agent such as paclitaxel, docetaxel, doxorubicin, and curcumin, quercetin, or natural extracts containing these active ingredients, and mixtures thereof. The fat-soluble active ingredient is included in the oil phase of the nanoemulsion formulation, solubilizing the active ingredient to enhance gastrointestinal absorption, thereby improving oral bioavailability and pharmacological activity.

The primary and secondary surfactants allow the inner aqueous phase in which the ion-pairing complex is dispersed to be dispersed in the oil phase, and allow the w/o primary nanoemulsion to be well dispersed in the external aqueous phase of the w/o/w secondary nanoemulsion. Preferably, the primary and secondary surfactants are any one or more each independently selected from the group consisting of poloxamer, caprylocaproyl polyoxyl-8 glycerides (Labrasol), Cremophor, caprylic/capric mono- and diglycerides (Capmul MCM), lauroyl polyoxyl-32 glycerides (Gelucire 44/14), Solutrol, polysorbate (Tween), and sorbitan monolaurate (Span).

The primary and secondary co-surfactants serve to reduce the surface energy so that the inner aqueous phase in which the ion-pairing complex is dispersed can be dispersed in the oil phase by the surfactant, and allow the w/o primary nanoemulsion to be well dispersed in the external aqueous phase of the w/o/w secondary nanoemulsion by the surfactant. The primary and secondary surfactants are any one or more each independently selected from the group consisting of diethylene glycol monoethyl ether (Transcutol HP), polysorbate, polyethylene glycol, butylene glycol, propylene glycol, ethanol, and isopropanol.

The mixture of the primary surfactant and the primary co-surfactant and the mixture of the secondary surfactant and the secondary co-surfactant are preferably included in an amount of 5 to 90% by weight, based on the total weight of the composition, more preferably 20 to 80% by weight. If the content is less than 20% by weight may reduce the stability of the emulsion, if it exceeds 80% by weight may cause irritation of the gastrointestinal mucosa. At this time, the content of the mixture of the primary surfactant and the primary co-surfactant and the mixture of the secondary surfactant and the secondary co-surfactant means the total amount of the primary and secondary surfactants and the primary and secondary co-surfactants in the total weight of the w/o/w secondary nanoemulsion including the secondary external aqueous phase.

Also, the primary and secondary co-surfactants are used in combination with the primary and secondary surfactants respectively, and the primary and secondary surfactants are preferably mixed in a weight ratio of 1:0.1 to 1:10 each independently, and more preferably in a ratio of 1:0.5 to 1:2.

Also, the present invention includes an oral delivery composition comprising oxaliplatin prepared according to the above method.

As the drug carrier of the ion-pairing complex of the oxaliplatin and bile acid derivatives according to the present invention, a multiple w/o/w nanoemulsion form may be used. The oil phase in this system protects the ion-pairing complexes in the gastrointestinal tract, minimizes the dilution effect of the absorption enhancer and enables high dispersibility of amphiphilic ion-pairing complexes in the gastrointestinal tract after taking. Multiple emulsified nanoemulsions are also known to enhance the absorption of drugs by modifying the structure and fluidity of the intestinal membrane in the gastrointestinal tract. Particularly, when 5-fluorouracil, a hydrophilic drug that cannot form an ion-pairing with a bile acid derivative, is supported on the inner aqueous phase together, the intestinal membrane permeability and oral bioavailability of drug can be improved by multiple emulsified nanoemulsions.

Also, the surfactants used in multiple emulsified nanoemulsions, Labrasol and Cremophor EL respectively disperse the primary internal aqueous phase in oil phase or can be used to disperse w/o primary nanoemulsion in the external aqueous phase of the w/o/w secondary nanoemulsion. Labrasol is known to interact with F-actin (filamentous actin) and ZO-1 (zonula occludens-1) to release tight junctions between small intestinal epithelial cells, and Cremophor EL was confirmed that not only increase the fluidity of the cell membrane but also promote the absorption by loosening the tight junction.

Therefore, the membrane permeability of the hydrophilic active ingredient 5-FU through the intercellular pathway can be increased by the application of a surfactant that induces a decrease in the binding between the small intestinal epithelial cells. Also Cremophor EL can bind to the hydrophobic region of P-gp, which results in morphological changes of P-gp, reducing the release of the drug into the intestinal tract, thereby limited gastrointestinal absorption rate of drugs released in P-gp medium, such as 5-FU, may be improved.

Hereinafter, the present invention will be described in more detail with reference to Examples. However, the following examples are provided to illustrate the present invention, but the scope of the present invention is not limited thereto.

Example 1: Preparation of Bile Acid Derivatives

Bile acid derivatives, oral absorption enhancers, were prepared by chemically bonding positively charged lysine with a to deoxycholic acid (DOCA).

H-Lys(Boc)-OMe.HCl in N-methylmorpholine (2.7%, w/v) was added to DOCA (2.6 g) in a solvent mixture of ethyl chloroformate (6.4 mL), N-methylmorpholine (7.4 mL), and THF (800 mL); the mixture was then refluxed for 2 h. After the reaction mixture was stirred overnight at room temperature, the precipitates were filtered and dried by removing solvent evaporation. Lys(Boc)DOCA was obtained by column chromatography of the precipitates with a solvent mixture of chloroform and methanol. The Lys (Boc)DOCA was further dissolved in a mixture of acetyl chloride and methanol in an ice bath. After the complete removal of the solvent, the residue was dissolved in water and washed with chloroform. Finally, the aqueous layer was gathered and freeze-dried to obtain DCK in powder form.

Example 2: Preparation of Ion-Pairing Complex of OXA with DCK (OXA/DCK)

Oxaliplatin and DCK prepared in Example 1 were dissolved respectively in deionized water with a pH 7.0 adjusted with sodium bicarbonate. While stirring the oxaliplatin aqueous solution, a DCK aqueous solution was slowly added to form an ion-pairing complex such that the molar ratio of oxaliplatin:DCK was 1:2. The mixed solution was centrifuged and freeze-dried at −70° C. to prepare a powdered OXA/DCK ion-pairing complex.

Example 3: Preparation of w/o Primary Nanoemulsions Comprising OXA/DCK Ion-Pairing Complex and 5-FU A two-step spontaneous emulsification method was employed to prepare w/o/w multiple emulsified nanoemulsions, and the first step was as follows.

The w/o primary nanoemulsion was constructed by an oil titration method using primary oil phase Capryol 90, a mixture of primary surfactant Labrasol and primary co-surfactant Transcutol HP ($S_{mix,1}$) and deionized water as aqueous phase.

Figure 1:
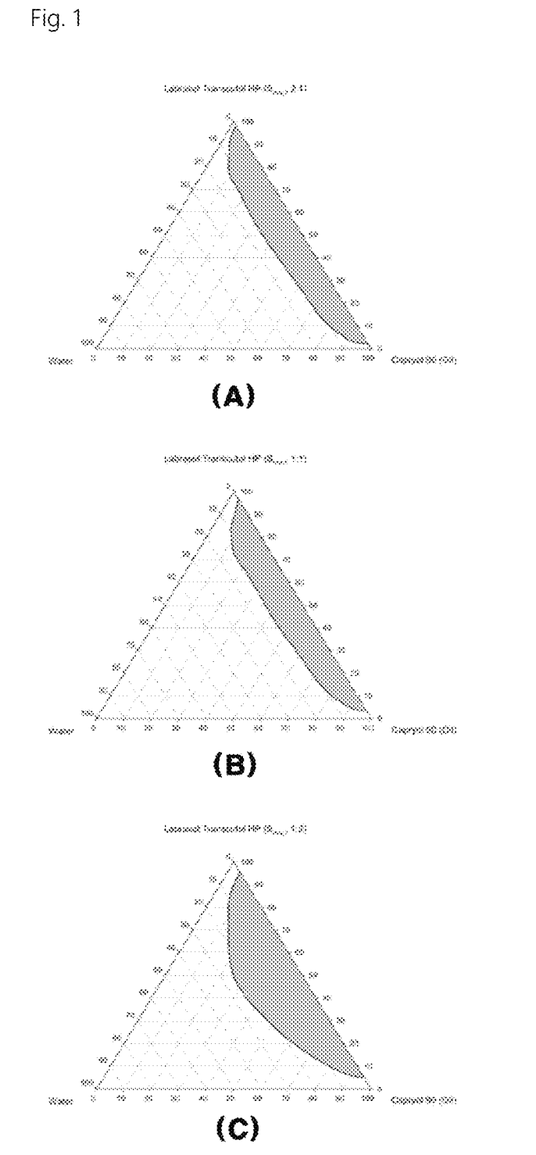
FIG. 1 shows pseudo-ternary phase diagram of w/o primary nanoemulsion regions for (A) $S_{mix, 1}$ 2:1, (B) $S_{mix, 1}$ (C) $S_{mix, 1}$ 1:2 according to Example 3 of the present invention.

The w/o primary nanoemulsion was identified as the region in the pseudo-ternary diagram where clear and transparent droplets were obtained based on visual observation, and a pseudo-ternary phase diagram of the w/o primary nanoemulsion region according to the mixing ratio (2:1, 1:1, 1:2) of $S_{mix,1}$ is shown in FIG. 1. From this region, the smallest sized internal aqueous droplet was formed and the maximum internal aqueous content was selected as the optimal w/o primary nanoemulsion composition: 21.4% aqueous phase, 50.0% primary surfactant and primary co-surfactant mixture ($S_{mix,1}$; Labrasol:Transcutol HP=1:2 (w/w)), 28.6% oil phase.

A pseudo-ternary diagram of the w/o primary nanoemulsion shown in FIG. 1 shows a w/o system comprising oil Capryol 90, primary surfactant Labrasol and the primary co-surfactant Transcutol HP in condition that the ratio of $S_{mix,1}$ is 2:1, 1:1 and 1:2. When the amount of the primary co-surfactant is added relatively less than the amount of the primary surfactant, for example when $S_{mix,1}$ is 2:1, the area of the w/o primary nanoemulsion is smaller than when $S_{mix,1}$ is 1:1, this means that the solubility of the oil phase by $S_{mix,1}$ is relatively low. When 42% of $S_{mix,1}$ 2:1 was added, the composition of the maximum aqueous phase which could be dispersed in the oil phase was found to be 13%, whereas the area where w/o primary nanoemulsion is formed at $S_{mix,1}$ 1:2, increased the ratio of co-surfactant to 1:2 in $S_{mix,1}$ has shifted to increase the amount of internal aqueous phase compared to $S_{mix,1}$ 1:1, and the composition of the aqueous phase, which could be dispersed in an oil phase of approximately 50% $S_{mix,1}$ 1:2, was 24%.

However, when the ratio of Transcutol HP, the primary co-surfactant in $S_{mix,1}$ was further increased compared to the primary surfactant, the w/o primary nanoemulsion formation region decreased. This means that the liquid crystalline phase was formed by Transcutol HP and not stabilized by the given amount of Labrasol. These results showed that the Gibbs free energy of nanoemulsion formulation may rely on the extent of which the primary surfactant and the primary co-surfactant passively reduce the interfacial tension at the w/o interface and the variation in dispersion entropy.

In the nanoemulsion area prepared by the $S_{mix,1}$ 1:2, several compositions were selected, the optimal w/o primary nanoemulsion composition was determined from the results of measuring the diameter and dispersion of aqueous phase droplets in emulsion (PDI), the content of aqueous phase in emulsion and permeable membrane permeability of drug: 21.4% aqueous phase (23.36% OXA or 67.52% OXA/DCK ion-pairing complex with 23.36% 5-FU), 50% mixture of Labrasol:Transcutol HP (1:2, w/w), and 28.6% Capryol 90.

Example 4: Preparation of w/o/w Secondary Nanoemulsions Comprising OXA/DCK Ion-Pairing Complex and 5-FU The w/o/w secondary nanoemulsion is composed of w/o primary nanoemulsion in the oil phase and a mixture of Cremophor EL and Transcutol HP was prepared as a mixture of a secondary surfactant and a secondary co-surfactant ($S_{mix,2}$) by titrating an oil phase in an aqueous phase.

Figure 2:
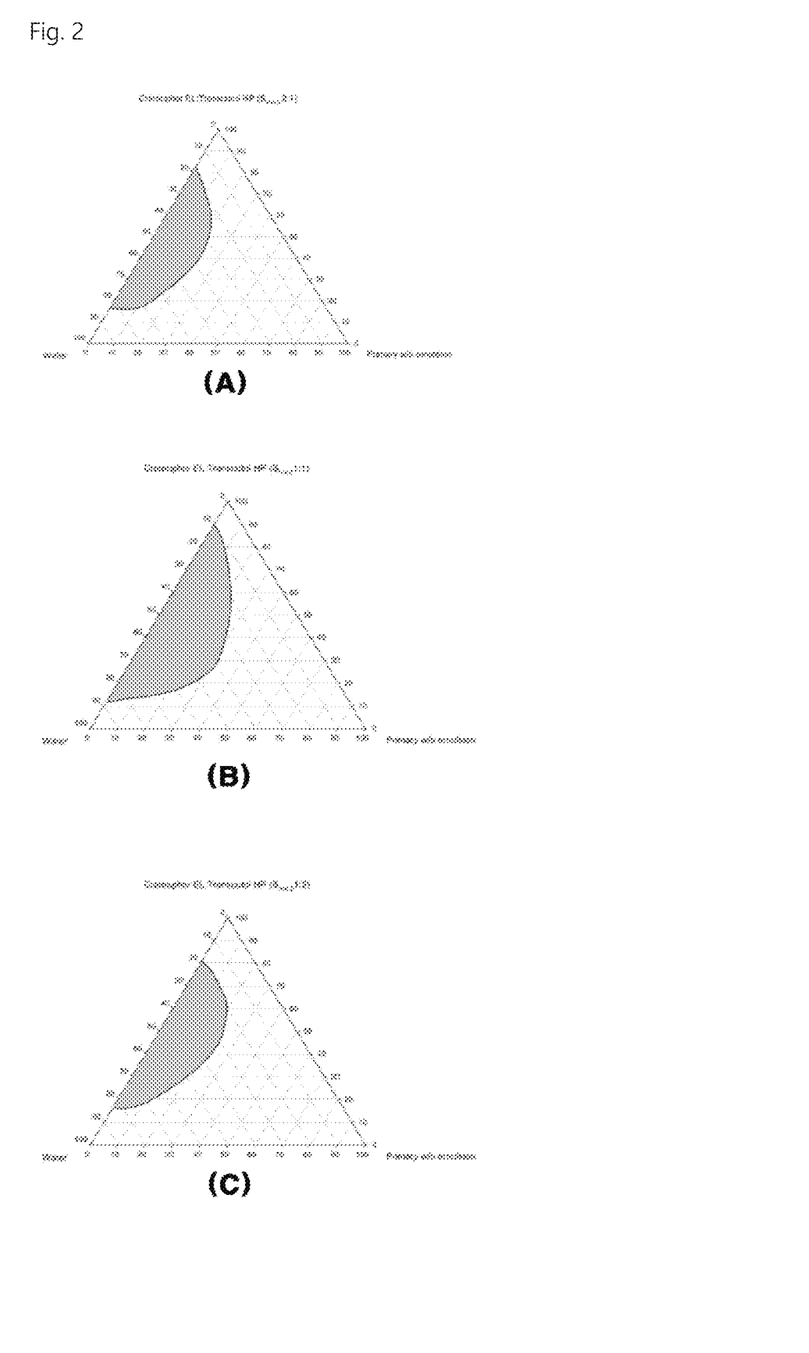
FIG. 2 shows pseudo-ternary phase diagram of w/o/w secondary nanoemulsion for (A) $S_{mix, 2}$ 2:1, (B) $S_{mix, 2}$ 1:1, (C) $S_{mix, 2}$ 1:2 according to Example 4 of the present invention.

23.36% OXA or 67.52% OXA/DCK ion-pairing complexes with 23.36% 5-FU were dispersed in the aqueous phase and then w/o primary nanoemulsion was prepared. Also, a mixture of $S_{mix,2}$ in a ratio of 2:1, 1:1, and 1:2 was mixed in a weight ratio of 1:9 to 9:1 in the w/o primary nanoemulsion prepared above, respectively. The final w/o/w secondary nanoemulsion was prepared by slowly adding deionized water to each mixture, and a pseudo ternary-phase diagram for w/o/w nanoemulsion with different $S_{mix,2}$ is shown in FIG. 2.

The area for w/o/w secondary nanoemulsion increased relatively with an increase in the total concentration of the secondary surfactant. $S_{mix,2}$ 1:1 increased the nanoemulsion region than $S_{mix,2}$ 2:1. The maximum amount of w/o primary nanoemulsion that was found to be dispersed in the external aqueous phase was 35% with a concentration of $S_{mix,2}$ 1:1 (29%). When the concentration of the co-surfactant was increased with respect to the surfactant ($S_{mix,2}$ 1:2), the nanoemulsion region decreased compared to $S_{mix,2}$ 1:1. The maximum amount of the w/o primary nanoemulsions dispersed 23% by 47% of $S_{mix,2}$ 1:2. As a result, when the ratio of the secondary co-surfactant increased compared to the secondary surfactant, it was confirmed that the nanoemulsion region was reduced.

Example 5: Confirmation of OXA/DCK Ion-Pairing Complex Formation

Figure 3:
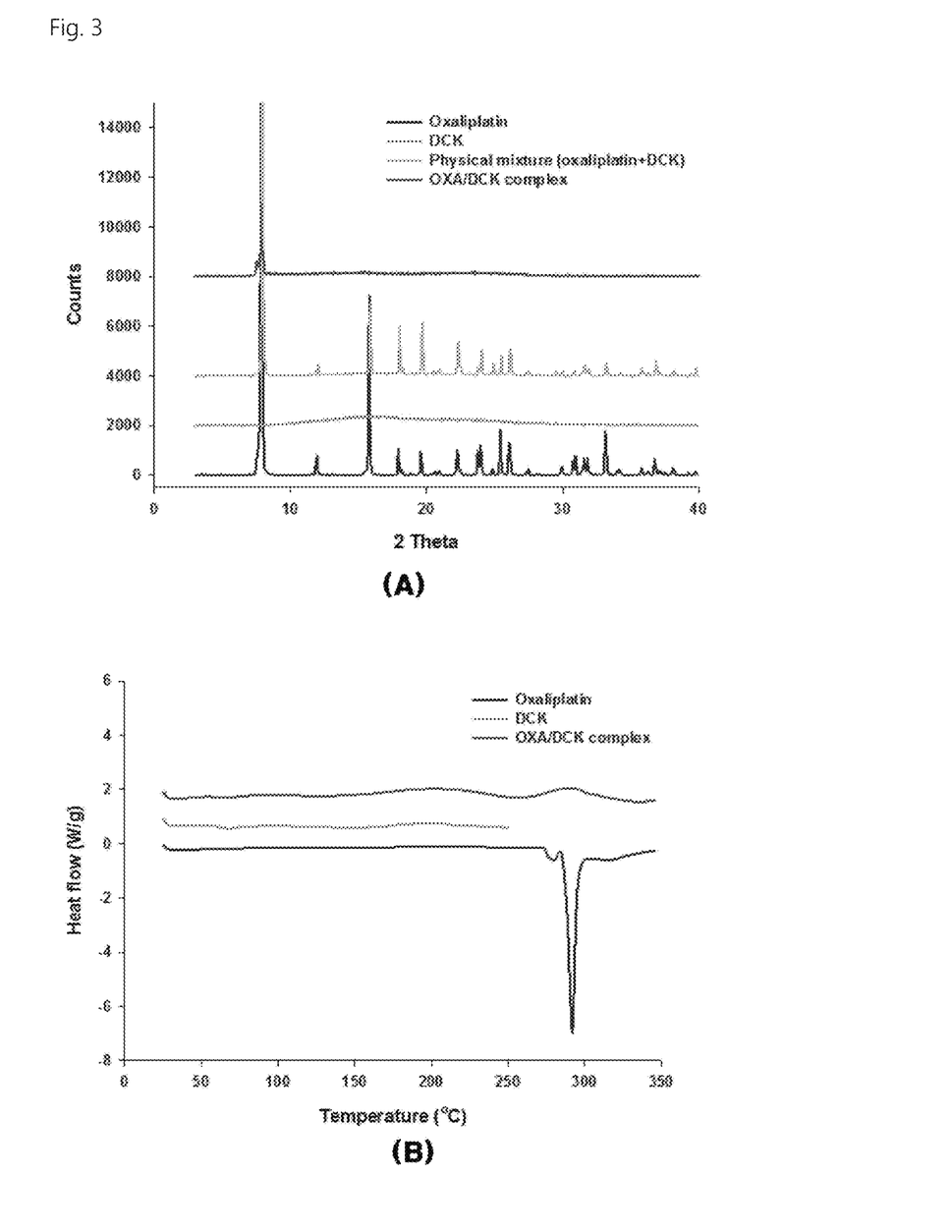
FIG. 3 shows (A) powder X-ray diffraction pattern, (B) differential scanning calorimetry thermogram according to Example 5 of the present invention.

To confirm the formation of ion-pairing complexes between oxaliplatin (OXA) and deoxycholic acid-lysine derivatives (DCK), the characteristic crystalline features of pure OXA, DCK, physical mixtures of OXA and DCK and OXA/DCK ionic complexes were analyzed using a powder X-ray diffraction (PXRD) and differential scanning calorimetry (DSC), and the results are shown in FIG. 3.

Pure OXA over the 2θ range of the PXRD spectrum show diffraction peaks for crystalline at 11.95°, 15.77°, 17.92°, 19.57°, 22.25°, 23.95°, 25.42°, 26.09°, 31.57°, 31.61°, 33.15°, and 36.76°, and showed characteristic diffraction peak for the crystalline OXA even in physical mixtures of OXA and DCK. This indicates that OXA in a mixture with DCK still existed in a crystalline form. However, no sharp diffraction peaks for crystalline OXA were seen in the OXA/DCK complex.

The characteristic endothermic peak were observed at 292° C. in the thermogram of the pure OXA, while it was absent from the DSC thermogram of the OXA/DCK complex. Therefore, it was found that OXA was molecularly dispersed with DCK to form a complex by ionic bonding and existed in an amorphous form after complex formation.

Example 6: Evaluation of Physicochemical Properties of w/o/w Secondary Nanoemulsions Containing OXA/DCK Ion-Pairing Complex and 5-FU After confirming the transparent nanoemulsion region from the pseudo-ternary phase diagram shown in FIG. 2, the physicochemical properties of the eight compositions selected from this region were evaluated. Average droplet size, polydispersity index (PDI) and zeta potential of w/o primary nanoemulsions dispersed in w/o/w secondary nanoemulsions comprising OXA/DCK ion-pairing complexes and 5-FU was measured by dynamic laser light scattering analyzer (Zetasizer Nano ZS90; Malvern Instruments, UK), and droplet morphology was observed by transmission electron microscopy (JEM-200; JEOL, Tokyo, Japan), which is shown in Table 1 and FIG. 4.

Figure 4:
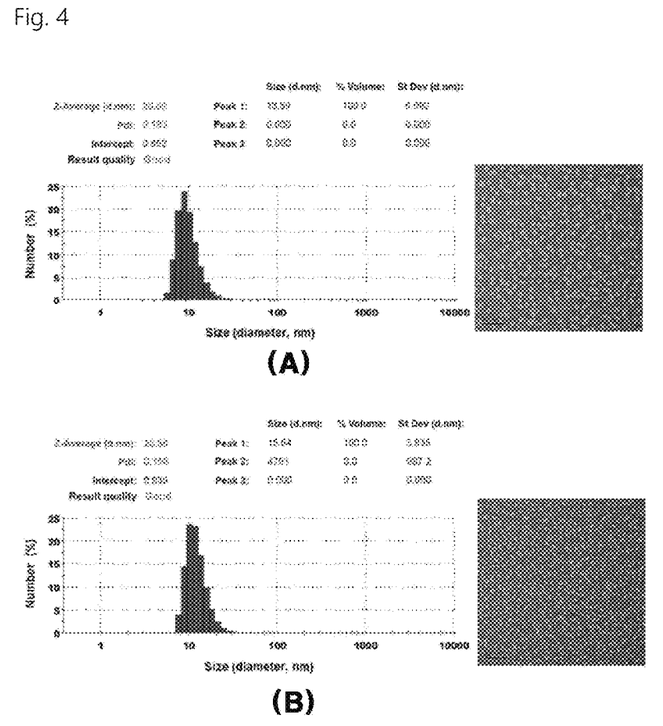
FIG. 4 shows a size distribution and TEM image of droplets in w/o/w secondary nanoemulsion composition E ($S_{mix, 2}$ 1:1) comprising (A) OXA or (B) OXA/DCK ion-pairing complexes according to Example 6 of the present invention.

In order to minimize the multiple scattering effect, each sample was diluted with deionized water (1:20), dispersed for 1 minute, and measured at 25° C. using a dynamic laser light scattering analyzer.

After diluting by 100 fold each sample with deionized water, one drop of the diluted solution was placed on a copper grid. After removing the excess liquid with paper filter, the sample was dyed with 2% aqueous solution of phosphotungstic acid, and the excess was removed with filter paper to measure transmission electron microscopy (TEM).

Referring to Table 1 below, the droplets sizes of the w/o primary nanoemulsion in the w/o/w secondary nanoemulsion at all compositions showed a uniform distribution with a PDI lower than 0.59, and the droplet size ranged from 13.5 nm to 232 nm.

The largest droplet size was observed in Composition A, where the composition of the w/o primary nanoemulsion dispersed in the w/o/w secondary nanoemulsion was maximum, and at each $S_{mix,2}$, it was observed that the dispersed droplet size increased rapidly as the concentration of the oil phase was increased from 10% to 30%. That is, the droplet sizes in Composition A and Composition C: 61.4±4.06 nm vs. 18.1±0.31 nm at $S_{mix,2}$ 2:1; 146±1.17 nm vs. 17.5±0.15 nm at $S_{mix,2}$ 1:1; 232±5.06 nm vs. 19.0±1.06 nm at $S_{mix,2}$ 1:2. These results indicate that the droplets size of the w/o primary nanoemulsion in the w/o/w secondary nanoemulsion is proportional to the concentration of the w/o primary nanoemulsion (oil phase) in the formulations. When the composition of the w/o primary nanoemulsion (oil phase) was constant at 20% or 30%, the droplet size decreased as the concentration of the secondary surfactant was increased. Therefore, it can be seen that the droplets size is maximized in the composition A including $S_{mix,2}$ 1:2 and 30% of w/o primary nanoemulsion (oil phase). However, the droplet size containing less than 10% w/o primary nanoemulsion (oil phase) was evaluated to be smaller than 20 nm regardless of the $S_{mix,2}$ ratio or its content.

Among w/o/w secondary nanoemulsion prepared with $S_{mix,2}$ 1:1, composition E were estimated to be 20.3±0.22 nm and 0.18±0.01 droplets and PDI respectively, and composition was found to produce the lowest mean droplet size compared to other formulations (13.5±0.14 nm).

The surface charge (zeta potential) values of all w/o/w secondary nanoemulsions were observed in the range of −4.65 mV to 0.14 mV (neutral), which means that the fatty acids and esters of the oil layer in the w/o primary nanoemulsions are covered and dispersed with the secondary surfactant and secondary co-surfactants in the w/o/w secondary nanoemulsions.

and were chromatographed using an isocratic mobile phase of deionized water (pH 3.2 adjusted with phosphoric acid) at a flow rate of 0.8 mL/min. The UV detection was carried out at 260 nm.

Effective permeability ($P_e$) of each drug was calculated using the following formula.

$$P_e = -\ln[1 - C_A(t)/C_{equilibrium}]/[A(1/V_D + 1/V_A) \times t]$$

($P_e$: permeability (cm/s); A: Effective filter area (f×0.3 cm$^2$; f: Porosity of the filter (f=0.76)); $V_D$: volume of the

TABLE 1

| w/o/w Secondary Nanoemulsion | | | Crempmophor EL:Transcutol HP ($S_{mix,2}$) | | | | | | | | |
|---|---|---|---|---|---|---|---|---|---|---|---|
| w/o | | | 2:1 | | | 1:1 | | | 1:2 | | |
| Primary Nano-Emulsion (%) | $S_{mix,2}$ (%) | Deionized water (%) | Droplets size (nm) | Dispersion | Zeta electric potential (mV) | Droplets Size (nm) | Dispersion | Zeta electric potential (mV) | Droplets size (nm) | Dispersion | Zeta electric potential (mV) |
| A | 30 | 30 | 40 | 61.4 (4.06) | 0.59 (0.01) | −2.03 (0.15) | 146 (1.17) | 0.30 (0.01) | −1.59 (0.12) | 232 (5.06) | 0.51 (0.04) | −0.80 (0.05) |
| B | 20 | 30 | 50 | 13.5 (0.11) | 0.03 (0.00) | −1.01 (0.13) | 22.6 (0.05) | 0.20 (0.00) | −3.48 (1.58) | 118 (1.97) | 0.31 (0.01) | −1.10 (0.32) |
| C | 10 | 20 | 70 | 18.1 (0.31) | 0.20 (0.01) | −0.27 (0.20) | 17.5 (0.15) | 0.18 (0.01) | 0.07 (0.52) | 19.0 (1.06) | 0.17 (0.02) | −0.42 (0.29) |
| D | 10 | 25 | 65 | 17.7 (1.08) | 0.08 (0.01) | −0.88 (0.24) | 16.8 (0.29) | 0.16 (0.01) | −0.04 (0.34) | 19.3 (0.44) | 0.16 (0.07) | 0.04 (0.35) |
| E | 10 | 30 | 60 | 14.5 (0.11) | 0.16 (0.01) | 0.14 (0.58) | 20.3 (0.22) | 0.18 (0.01) | −4.65 (1.68) | 18.3 (0.60) | 0.20 (0.01) | −0.13 (0.30) |
| F | 10 | 35 | 55 | 17.5 (0.19) | 0.20 (0.00) | −0.86 (0.40) | 13.6 (0.04) | 0.04 (0.01) | −0.04 (0.34) | 15.0 (0.58) | 0.08 (0.05) | −0.53 (0.09) |
| G | 10 | 40 | 50 | 18.0 (0.21) | 0.14 (0.01) | −1.16 (0.25) | 20.0 (0.20) | 0.20 (0.00) | −1.59 (0.12) | 15.0 (0.58) | 0.04 (0.01) | 0.14 (0.49) |
| H | 10 | 60 | 30 | 14.1 (0.06) | 0.14 (0.01) | −1.01 (0.58) | 13.5 (0.14) | 0.05 (0.01) | −4.36 (1.13) | 14.0 (0.16) | 0.03 (0.01) | −0.11 (0.34) |

Figure 5:
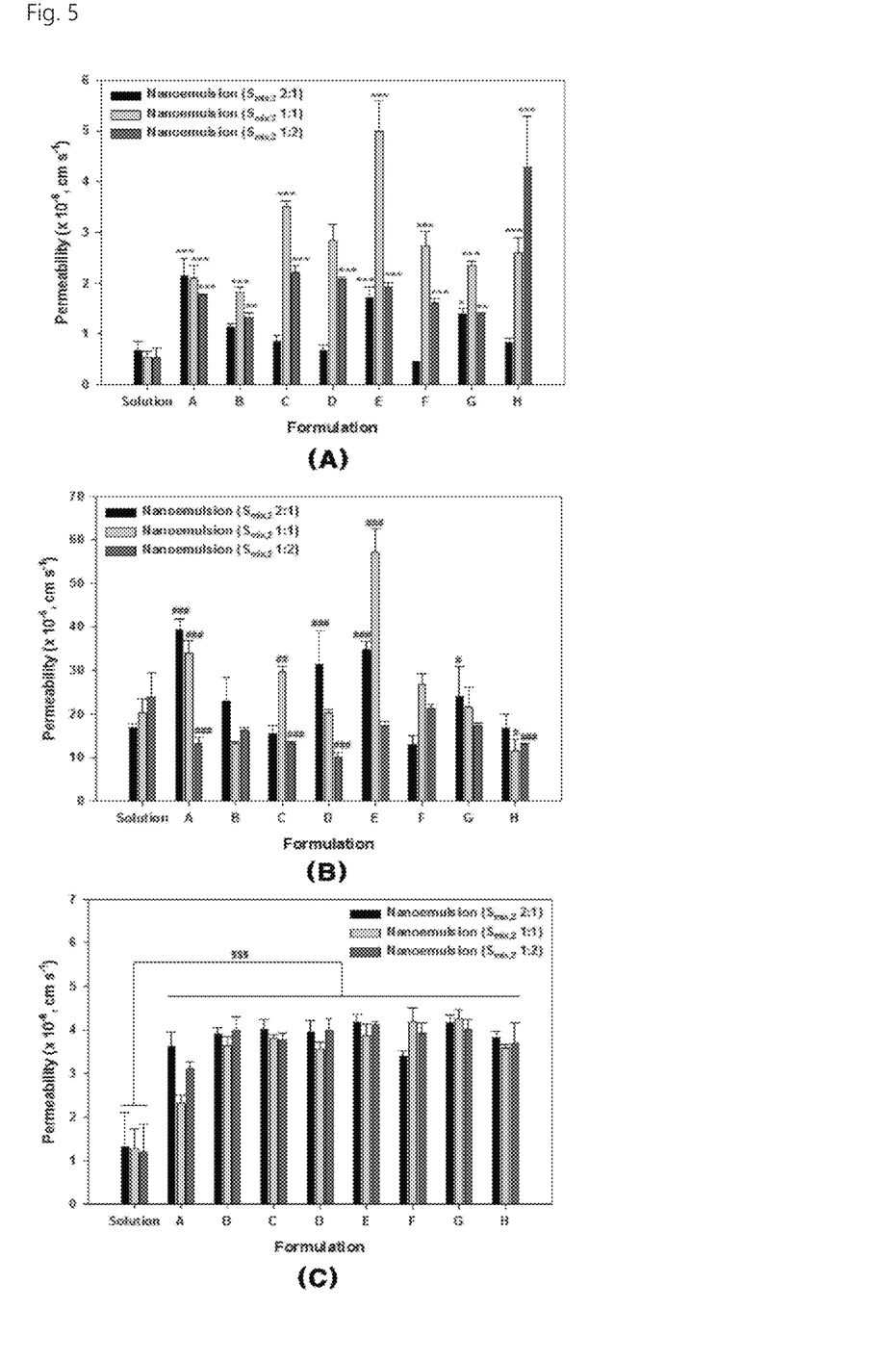
FIG. 5 shows the artificial intestinal membrane permeability of (A) OXA, (B) OXA/DCK ion-pairing complex, (C) OXA/DCK ion-pairing complex according to Example 7 of the present invention.

Example 7: Determination of the Intestinal Membrane Permeability of w/o/w Secondary Nanoemulsions Containing OXA/DCK Ion-Pairing Complex and 5-FU Membrane permeability of w/o/w secondary nanoemulsions containing OXA, OXA/DCK ion-pairing complex or 5-FU, respectively, prepared in the composition of Table 1 above was evaluated using an artificial intestinal membrane (PAMPA; BD Biosciences, San Jose, Calif., USA), and as a control, OXA, OXA/DCK ion-pairing complex and 5-FU aqueous solution were used, and the results are shown in FIG. 5.

Each sample was diluted with phosphate-buffer (PBS, pH 6.8) at the concentration of 125.8 μM OXA, 125.8 μM OXA/DCK ion-pairing complex, and 384.4 μM 5-FU. Then, 200 μL was added to the donor of each well of the PAMPA plate, and 300 μL of buffer (PBS, pH 6.8) was added to each well of the receptor plate. The plate assembly was set by coupling the donor plate with the receiver plate. After 5 hours at room temperature, samples were withdrawn from donors and receptors in each well of the PAMPA plate, and the concentration was measured as follows.

OXA or OXA/DCK ion-pairing complexes were analyzed by HPLC using a C18 column (4.6×250 mm, 5 μm, 100 Å; 20 μL injection) at 40° C. The mobile phase consisted of water (pH 3.0 adjusted with phosphoric acid)-acetonitrile (99:1, v/v) and was run at a flow rate of 0.8 mL/min. OXA or OXA/DCK was measured using a UV detector at 210 nm.

For 5-FU, injected into an HPLC system equipped with a C18 column (4.6×250 mm, 5 μm, 100 Å; 20 μL injection), donor well (0.2 mL); $V_A$: volume of Receptor well (0.3 mL); t: the total time of incubation in seconds (s); $C_A(t)$: concentration of drug in the receptor well at time t; $C_{equilibrium}$: [$C_D(t) \times V_D + C_A(t) \times V_A$]/($V_D + V_A$); $C_D(t)$: concentration of residual drug in donor at time t)

As a result, the artificial intestinal membrane permeability of OXA, OXA/DCK ion-pairing complex and 5-FU was significantly increased after inclusion in the inner phase of the w/o/w multiple nanoemulsion as a whole.

In the case of OXA, the membrane permeability was influenced by the secondary surfactant to secondary co-surfactant ratio ($S_{mix,2}$) and $S_{mix,2}$ to oil phase (w/o primary nanoemulsion) ratio. Except for composition H, the permeability value of OXA w/o/w multiple nanoemulsion prepared by $S_{mix,2}$ 1:1 was relatively higher than those from the compositions with $S_{mix,2}$ 2:1 and 1:2 at the same composition. In w/o/w multiple nanoemulsions containing 10% oil phase, when the $S_{mix,2}$ 1:1 to oil phase ratio was increased from 2 to 6 at 10% of the oil phase (composition C to H), the maximum membrane permeability of OXA was observed in the composition E ($S_{mix,2}$ 1:1 to oil phase ratio 1:3), where the membrane permeability of OXA (4.99±0.59 (×10$^{-6}$), cm/s) was about 9.24-fold greater than the permeability of the aqueous OXA solution (0.54±0.12 (×10$^{-6}$), cm/s)).

However, the permeability of OXA/DCK ion-pairing complexes was still 37.4- and 4.02-fold higher than OXA aqueous solution and OXA w/o/w multiple nanoemulsion composition E ($S_{mix,2}$ 1:1) respectively. At $S_{mix,2}$ 2:1, where the proportion of surfactant is greater than the co-surfactant, the intestinal membrane permeability of the OXA/DCK ion-pairing complex was relatively higher than permeability of the nanoemulsion with high or low oil phase (w/o primary nanoemulsion) content. While the membrane permeability of OXA/DCK ion-pairing complex was not significantly improved by incorporating $S_{mix,2}$ 1:2 at the same composition. Intestinal membrane permeability of the OXA/DCK ion-pairing complex from w/o/w multiple nanoemulsion E ($S_{mix,2}$ 1:1) showed the maximum, and the permeability value was 2.85 and 1.46 times greater than those from the solution and w/o/w multiple nanoemulsion A ($S_{mix,2}$ 2:1), respectively. Moreover, OXA/DCK ion-pairing complex membrane permeability (57.2±5.23 (×10$^{-6}$), cm/s) from composition E ($S_{mix,2}$ 1:1) was 107- and 11.5-fold greater than the permeability of OXA from OXA aqueous solution (0.54±0.12 (×10$^{-6}$), cm/s) and composition E (4.99±0.59 (×10$^{-6}$), cm/s) respectively.

In the case of 5-FU, the permeability from the compositions C to H did not show a large difference due to the same oil phase content and similar droplet size, and the membrane permeability of 5-FU increased as the amount of oil phase decreased at all $S_{mix,2}$ ratios. Membrane permeability (3.78±0.26 (×10$^{-6}$), cm/s) of 5-FU from composition E ($S_{mix,2}$ 1:1) was 3.05-fold greater than that of 5-FU aqueous solution (1.27±0.46 (×10$^{-6}$), cm/s).

Example 8: In Vitro Intestinal Cell Membrane Permeability Measurement of w/o/w Secondary Nanoemulsions Comprising OXA/DCK Ion-Pairing Complex and 5-FU Membrane permeability of the w/o/w secondary nanoemulsion containing OXA, OXA/DCK ion-pairing complex or 5-FU respectively prepared in the composition of Table 1, was evaluated using Caco-2 cell monolayer, and as a control OXA, OXA/DCK ion-pairing complex and 5-FU aqueous solution were used, and the results are shown in Table 2 below.

Caco-2 cells were seeded onto each well of 12-well Transwell® filter insert (pore size: 0.4 μm, surface area: 1.12 cm$^2$; Corning, N.Y., USA) at a density of 3×10$^5$ cells/well. Dulbecco's modified Eagle's medium (DMEM; Lonza, Basel, Switzerland) medium containing 10% fetal bovine serum (FBS; Gibco, Thermo Fisher Scientific) and 1% penicillin/streptomycin (Gibco) was changed every 48 hours for 21 to 29 days, and Caco-2 cell monolayers with a transepithelial electrical resistance (TEER) of >350 Ω·cm$^2$ were used for in vitro intestinal membrane permeability experiments.

First, the culture medium was removed and the monolayer was pre-incubated with 0.5 mL of Hanks' balanced salt solution (HBSS) for 20 min at 37° C. After measuring the TEER, the HBSS was removed; and 0.5 mL of 125.8 μM OXA, 125.8 μM OXA/DCK, and 384.4 μM 5-FU in HBSS or nanoemulsion diluted with HBSS, and 1.5 mL of HBSS were added to the each apical and basolateral compartment, respectively and incubated at 37° C. After processing the sample, 100-μL samples were taken from the basolateral compartment at 0.5, 1, 2, 3, 4, and 5 h. The samples were filtered through a membrane filter. The concentration of OXA, OXA/DCK complex, or 5-FU permeated though the monolayer was determined using the HPLC system with a UV detector, as in Example 7.

Also, the apparent permeability coefficient ($P_{app}$) of OXA, OXA/DCK ion-pairing complex or 5-FU was calculated according to the following equation.

$$P_{app}=dQ/dt \times 1/(A \times C_0)$$

(dQ/dt: the linear appearance rate of mass in the basolateral sides (μmoL/s),
$C_0$: initial concentration of OXA, OXA/DCK complex, or 5-FU on the apical side (μmoL/mL),
A: the surface area of the monolayer (cm$^2$).

Referring to Table 2 below, when OXA was formulated in nanoemulsion E ($S_{mix,2}$ 1:1), $P_{app}$ of OXA increased from 2.50±1.96 (×10$^{-6}$, cm/s) to 7.08±1.42 (×10$^{-6}$, cm/s).

Also, the permeability of OXA was significantly improved compared to the aqueous OXA solution by ionic complex formation with DCK. When OXA/DCK ion-pairing complexes are included in nanoemulsion E (12.0±1.91 (×10$^{-6}$), cm/s), the apical-to-basal $P_{app}$s of OXA/DCK ionic complexes were further enhanced 2.13- and 4.80-fold compared to OXA alone (5.63±3.03 (×10$^{-6}$), cm/s) and OXA/DCK ionic complexes (2.50±1.96 (×10$^{-6}$), cm/s).

The membrane permeability of 5-FU was also significantly increased by incorporation of 5-FU into the nanoemulsion, and the permeability of 5-FU (14.9±3.08 (×10$^{-6}$), cm/s) in Composition E ($S_{mix,2}$ 1:1) is increased 4.30-fold compared to 5-FU aqueous solution (3.46±1.22 (×10$^{-6}$), cm/s).

Also, the permeability of OXA, OXA/DCK ion-pairing complex or 5-FU nanoemulsion across Caco-2 cell monolayer displayed a tendency to increase as the weight ratio of $S_{mix,2}$ to oil phase increased from 1:1 to 1:3, and then significantly decreased at the ratio of 1:6.

TABLE 2

| | $S_{mix,2}$1:1/oil phase (w/w) | Apparent permeability ($P_{app}$, ×10$^{-6}$ cm/s) | | |
|---|---|---|---|---|
| | | OXA | OXA/DCK | 5-FU |
| Solution | — | 2.50 ± 1.96 | 5.63 ± 1.03 | 3.46 ± 1.22 |
| C | 2 | 7.54 ± 1.40 | 11.6 ± 1.13 | 5.90 ± 2.46 |
| E | 3 | 7.08 ± 1.42 | 12.0 ± 1.91 | 14.9 ± 3.08 |
| F | 3.5 | 7.40 ± 2.02 | 10.5 ± 0.81 | 10.6 ± 1.77 |
| G | 4 | 2.10 ± 0.61 | 10.1 ± 0.73 | 8.15 ± 3.90 |
| H | 6 | 1.77 ± 0.37 | 8.93 ± 1.32 | 7.49 ± 0.36 |

Example 9: Drug Release Test of w/o/w Secondary Nanoemulsions Containing OXA/DCK Ion-Pairing Complex and 5-FU Dissolution tests were performed in 500 mL of medium containint 0.1 N HCl solution (pH 1.2) or phosphate buffer (pH 6.8) at 37±0.2° C., using the USP type 1 apparatus (basket) rotating at 100 rpm.

Ten milligrams of OXA or 38.8 mg of OXA/DCK complex (equivalent to 10 mg of OXA) with 10 mg of 5-FU powder or in 800 mg of w/o nanoemulsions with $S_{mix,2}$ (formulations C, E, F, G, and H without secondary aqueous phase) were encased in a hard gelatin capsule size 00. Each capsule was subjected to a dissolution test, and 1-mL samples were withdrawn at 15, 30, 45, 60, 90, and 120 min. After filtration, the amount of drug released was quantified by the HPLC using a UV detector, as in Example 7, and the results are shown in FIG. 6.

Figure 6:
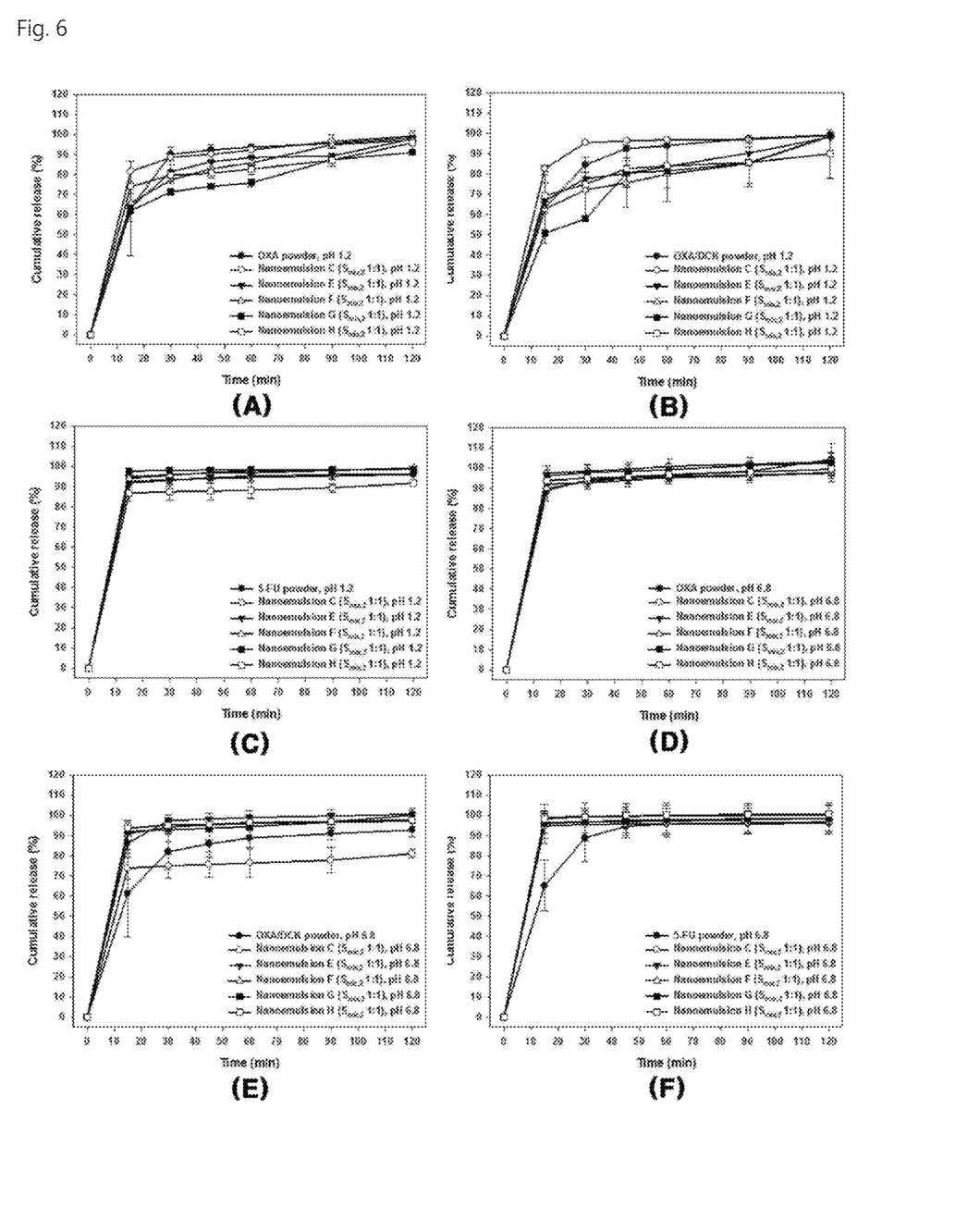
FIG. 6 shows the cumulative drug release of (A) OXA, (B) OXA/DCK ion-pairing complex, (C) 5-FU at pH 1.2 conditions, and the cumulative drug release of (D) OXA, (E) OXA/DCK ion-pairing complex, (F) 5-FU at pH 6.8 conditions, according to Example 9 of the present invention.

As shown in FIGS. 6(A) and (B), at pH 1.2, more than 90% of the OXA or OXA/DCK ion-pairing complexes were released from the nanoemulsion within 120 minutes. However, the dissolution rates of OXA or OXA/DCK ionic complexes from nanoemulsions G and H were relatively delayed compared with the powder form or the other nanoemulsion compositions.

In contrast, at least 85% of 5-FU was released from the nanoemulsions within 15 min, and the dissolution rate of 5-FU at pH 1.2 was not significantly influenced by incorporating it in the nanoemulsion (FIG. 6(C)).

Referring to FIGS. 6(D) and (F), at least 90% of OXA and 5-FU were completely released from the nanoemulsion within 15 min. at pH 6.8.

OXA/DCK ion-pairing complex capsules filled in powder form represented a delayed release compared with release from the nanoemulsion (except composition C). More than 90% of OXA/DCK ionic complex released from the nanoemulsion within 15 min except composition C. This may have resulted from aggregation of the conjugated DCK molecules in the complex, as well as a lower $S_{mix,2}$ to oil (the primary w/o emulsion) ratio.

Example 10: In Vivo Oral Absorption Evaluation of w/o/w Secondary Nanoemulsions Containing OXA/DCK Ion-Pairing Complex and 5-FU To evaluate the improvement in oral absorption of OXA and 5-FU due to the formation of ionic complexes with bile acid derivatives and formulation as a nanoemulsion, an aqueous solution comprising OXA or OXA/DCK ion-pairing complex incorporated with 5-FU in the nanoemulsion comprising the same (composition E in Table 1, $S_{mix,2}$ 1:1) were orally administered to rats.

Figure 7:
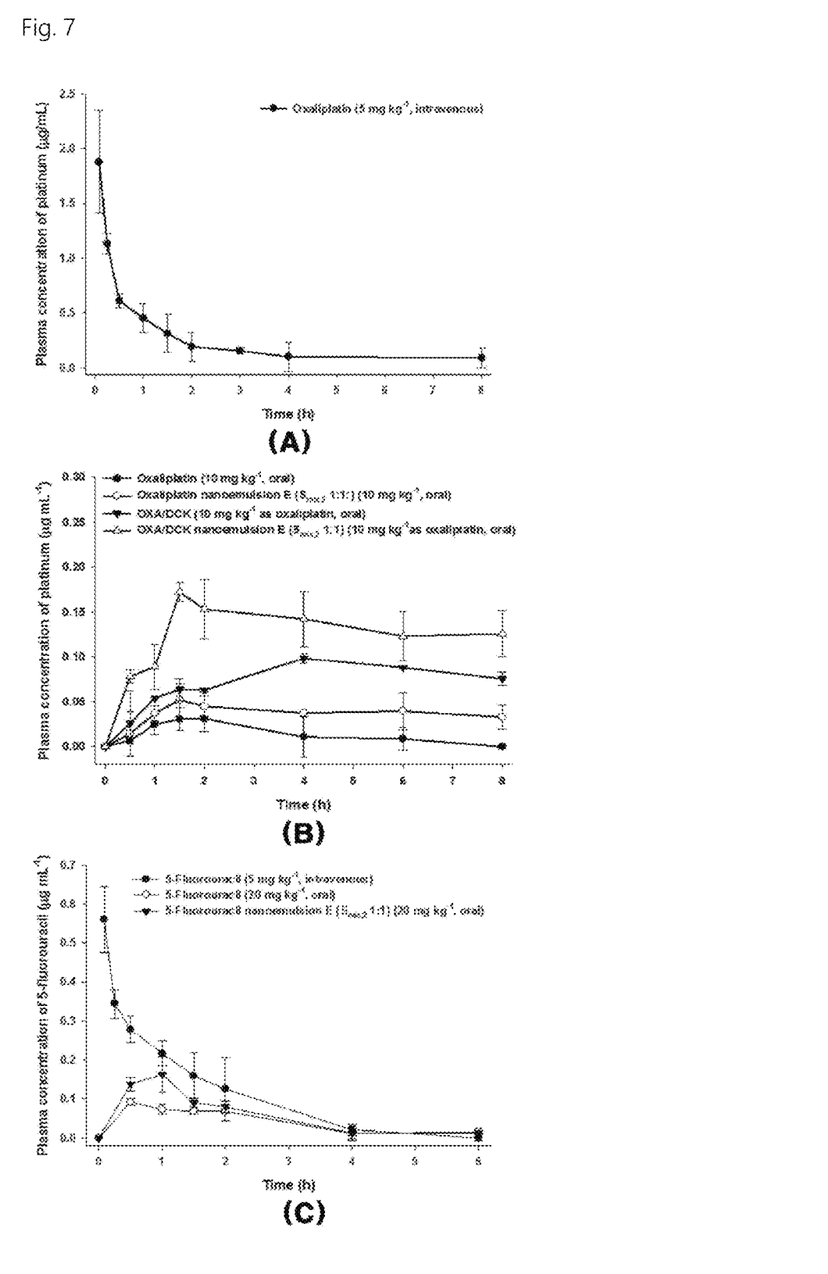
FIG. 7 shows, in rat according to Example 10 of the present invention, (A) drug concentration in blood over time after OXA intravenous injection (B) drug concentration in blood over time after oral administration of secondary nanoemulsions comprising OXA, OXA/DCK ion-pairing complexes and OXA/DCK ion-pairing complexes, (C) drug concentration in blood over time after 5-FU intravenous infusion and after oral administration of a secondary nanoemulsion containing 5-FU or 5-FU.

FIG. 7, Table 3 and Table 4 below show the drug concentration in blood-time profiles of rats and the pharmacokinetic parameters of OXA and 5-FU.

Each rat was orally administered 400 μL of aqueous solution consisting of OXA (10 mg/kg), OXA/DCK ionic complex (equivalent to 10 mg/kg of OXA), or 5-FU (20 mg/kg), as well as a 400-μL nanoemulsion diluted with water to comprise OXA (10 mg/kg) or OXA/DCK ionic complex (equivalent to 10 mg/kg of OXA) with and 5-FU (20 mg/kg). To evaluate oral bioavailability, 150 μL of OXA (5 mg/kg) or 5-FU (5 mg/kg) in aqueous solutions were also injected via the tail vein.

After oral and intravenous administration, 200 μL of blood was collected from a capillary in the retro-orbital plexus at different time intervals and directly mixed with 50 μL of sodium citrate (3.8% solution). Blood samples were then immediately centrifuged (2,500×g, 15 minutes, 4° C.). The plasma samples were isolated and kept frozen at −70° C. until analysis.

The plasma concentration of OXA was estimated by the Pt concentration using atomic absorption spectroscopy (AAS) after the plasma collected for analysis was diluted with 5 mL of nitric acid and heated for 6 h in a 100° C. Before analysis, the sample was diluted with 10 mL of 3% nitric acid solution and then injected into the furnace for AAS analysis. All measurements were carried out using a Thermo Scientific iCE 3500 AAS (Thermo Fisher Scientific) equipped with a GFS35 graphite furnace and a GFS35Z autosampler. Argon was used as the purging gas at 200 mL/min, and the injection volume of the sample was 20 μL. The spectrometer was provided with a Zeeman-based background corrector, and the platinum concentration was 266 nm.

To determine the plasma concentration of 5-FU, 100 μL of each standard and plasma samples were diluted with 50 μL of 20 μg/mL internal standard (IS, chlorouracil) and 100 μL of saturated ammonium sulfate solution. After vortexing for 1 min, the diluted plasma sample was extracted with a 2-mL solvent mixture of propanol and diethylether (80:20, v/v). The mixture was then centrifuged at 2,500×g for 10 min and the collected organic phase was evaporated under nitrogen at 37° C. The dried residues were reconstituted with 100 μL of mobile phase for HPLC analysis (ammonium phosphate buffer with pH 6.8/methanol, 98:2, v/v), followed by vortexing, and then determined by HPLC with a C8 column (4.6×250 mm, 5 μm) at a flow rate of 1 mL/min mobile phase. A 50-μL sample was injected and 5-FU was measured at 260 nm.

The oral absorption rate of OXA also increased significantly after inclusion in the nanoemulsion, resulting in a 1.66- and 2.67-fold increase in the $C_{max}$ and $AUC_{last}$ respectively. However, the oral absorption rate of OXA was more enhanced by ionic complex formation with DCK, and the $C_{max}$ and $AUC_{last}$ values for OXA/DCK ion-pairing complex were 306% and 540% improved, respectively, compared to the OXA aqueous solution.

As also shown in FIG. 7, the $C_{max}$ and $AUC_{last}$ values for nanoemulsions containing OXA/DCK ion-pairing complexes were 1.77- and 1.70-fold greater than the OXA/DCK ion-pairing complex aqueous solutions, respectively, as well as 5.41- and 9.17-fold greater compared to OXA aqueous solution. Also referring to Table 3 below, the oral bioavailability of the nanoemulsion comprising the OXA/DCK ion-pairing complex was 9.19-fold higher than the oral bioavailability of the simple OXA aqueous solution due to the ionic complexed DCK molecules and nanoemulsification.

TABLE 3

|  | OXA | | | OXA/DCK | |
|---|---|---|---|---|---|
|  | Solution | Solution | Nanoemulsion | Solution | Nanoemulsion |
| Route of administration | Intravenous | Oral | Oral | Oral | Oral |
| OXA dosage (mg/kg) | 5 | 10 | 10 | 10 | 10 |
| $T_{max}$ (h) | — | 1.833 ± 0.289 | 2.333 ± 1.443 | 4.000 ± 0.000 | 1.667 ± 0.289 |
| $T_{1/2}$ (h) | 3.103 ± 2.114 | 1.528 ± 0.900 | 11.466 ± 6.708 | 10.512 ± 1.625 | 17.616 ± 2.639 |
| $C_{max}$ (μg/mL) | 2.454 ± 0.990 | 0.032 ± 0.014 | 0.053 ± 0.017 | 0.098 ± 0.005 | 0.173 ± 0.012 |
| $AUC_{last}$ (μg · h/mL) | 1.962 ± 0.746 | 0.111 ± 0.095 | 0.296 ± 0.093 | 0.600 ± 0.046 | 1.018 ± 0.204 |
| $AUC_{inf}$ (μg · h/mL) | 2.537 ± 1.312 | 0.170 ± 0.061 | 0.924 ± 0.621 | 1.755 ± 0.333 | 4.198 ± 0.876 |
| Bioavailability (%) | 100 | 2.824 ± 2.428 | 7.543 ± 2.359 | 15.290 ± 1.182 | 25.951 ± 5.190 |

{In Table 3, $T_{max}$ Time to reach $C_{max}$; $T_{1/2}$: Plasma concentration half-life; $C_{max}$: Maximum plasma concentration; $AUC_{last}$: Area under the plasma concentration-time curve up to the time of the last measurable plasma concentration measurement; $AUC_{inf}$: Area under the plasma concentration-time curve to infinity}

As shown in Table 4 below, the $C_{max}$ value of 5-FU nanoemulsion, 0.164±0.044 μg/mL, was 1.78-fold higher than that of 5-FU solution (0.092±0.008 μg/mL).

Also, The $AUC_{last}$ value for the 5-FU nanoemulsion also increased by 1.39-fold compared to that of the 5-FU solution (0.242±0.058 μg·h/mL). Thus, the resulting oral bioavailability of the 5-FU nanoemulsion was evaluated as a 139% increase compared with that of free 5-FU.

TABLE 4

|  | 5-FU solution | 5-FU solution | 5-FU nanoemulsion |
|---|---|---|---|
| Administration | Intravenous | Oral | Oral |
| 5-FU dose (mg/kg) | 5 | 20 | 20 |
| $T_{max}$ (h) | — | 0.500 ± 0.000 | 0.833 ± 0.289 |
| $T_{1/2}$ (h) | 0.760 ± 0.109 | 0.813 ± 0.567 | 1.386 ± 0.146 |
| $C_{max}$ (μg/mL) | 0.716 ± 0.124 | 0.092 ± 0.008 | 0.164 ± 0.044 |
| $AUC_{last}$ (μg·h/mL) | 0.657 ± 0.220 | 0.242 ± 0.058 | 0.337 ± 0.089 |
| $AUC_{inf}$ (μg·h/mL) | 0.670 ± 0.221 | 0.287 ± 0.096 | 0.360 ± 0.091 |
| Bioavailability (%) | 100 | 9.218 ± 2.198 | 12.808 ± 3.403 |

{In Table 4, $T_{max}$: $C_{max}$: Time to reach; $T_{1/2}$: Plasma concentration half-life; $C_{max}$: Maximum plasma concentration; $AUC_{last}$: Area under the plasma concentration-time curve up to the time of the last measurable plasma concentration measurement; $AUC_{inf}$: Area under the plasma concentration-time curve to infinity}

Example 11: In Vivo Tumor Growth Inhibition Efficacy Evaluation of w/o/w Secondary Nanoemulsions Containing OXA/DCK Ion-Pairing Complex and 5-FU The CT26 mouse colon tumor cells were subcutaneously grafted into the flanks of BALB/c mice at a concentration of 1×10⁶ cells/100 μL of PBS (pH 7.4). On day 14, when each tumor size was 70-100 mm³, mice were randomly divided into five groups of 10 animals each: Control (not treated); OXA-S (once daily oral administration of 10 mg/kg OXA in water); OXA/DCK-S (once daily oral administration OXA/DCK complex as 10 mg/kg OXA in water); 5-FU-S (once daily oral administration of 10 mg/kg 5-FU in water); OXA/DCK-5FU-NE (once daily oral administration nanoemulsion [formulation E] containing OXA/DCK complex as 10 mg/kg OXA and 10 mg/kg 5-FU); groups. During 18-day treatment, mice were fasted for 4 h before oral administration and 2 h after administration. Tumors were measured every three days in two dimensions using a caliper, and tumor volumes were calculated as $a^2×b×0.52$, where a=width and b=length. Body weight was also measured.

Figure 9:
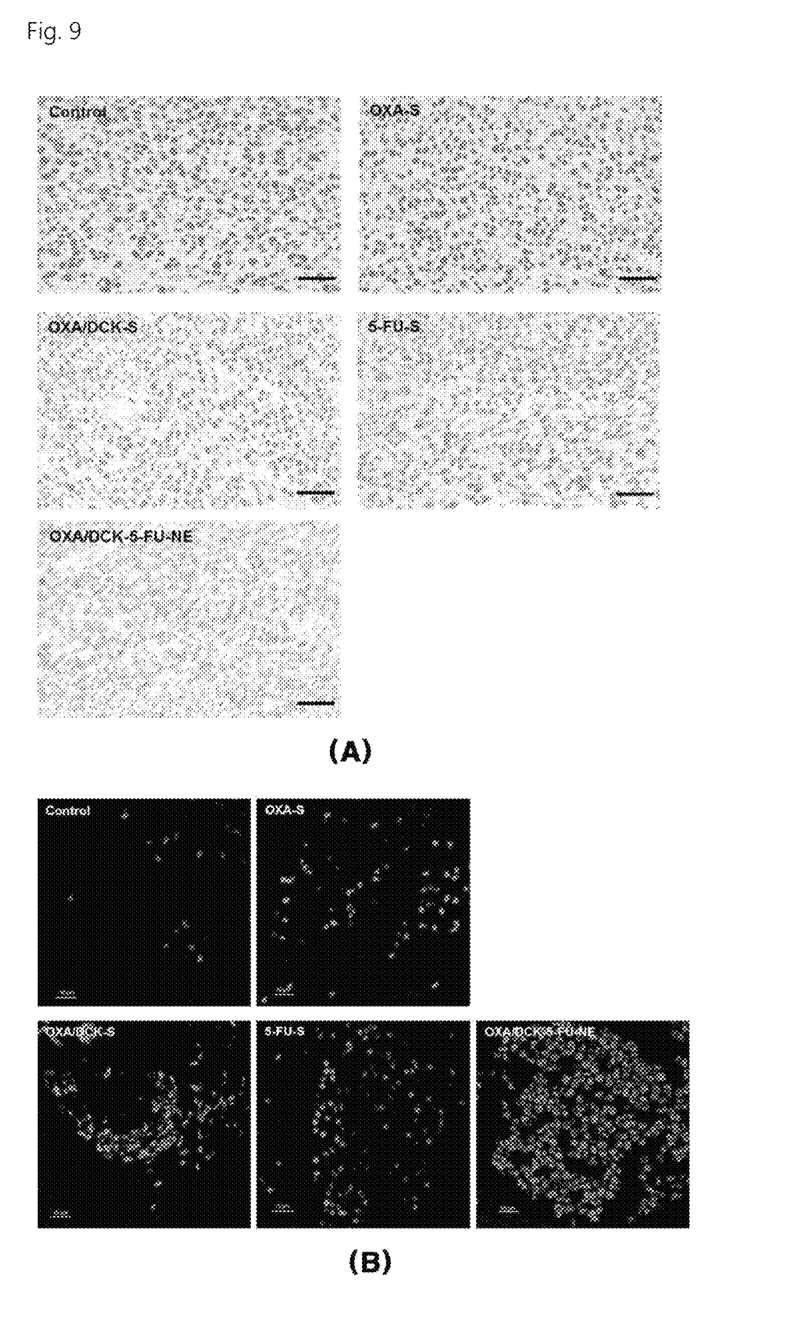
FIG. 9 shows, according to Example 11 of the present invention, a cross-sectional image of (A) PCNA and (B) TUNEL stained extracted tumor tissue sections.

At 18 days after administration, the isolated tumors masses were measured, and tumor tissues were fixed in 10% formalin for histological evaluation. Staining with proliferating cell nuclear antigen (PCNA) for cell proliferation and fluorescent terminal deoxynucleotidyl transferase-mediated dUPT nick end labeling (TUNEL) for apoptosis were carried out. The results are shown in FIG. 9.

Figure 8:
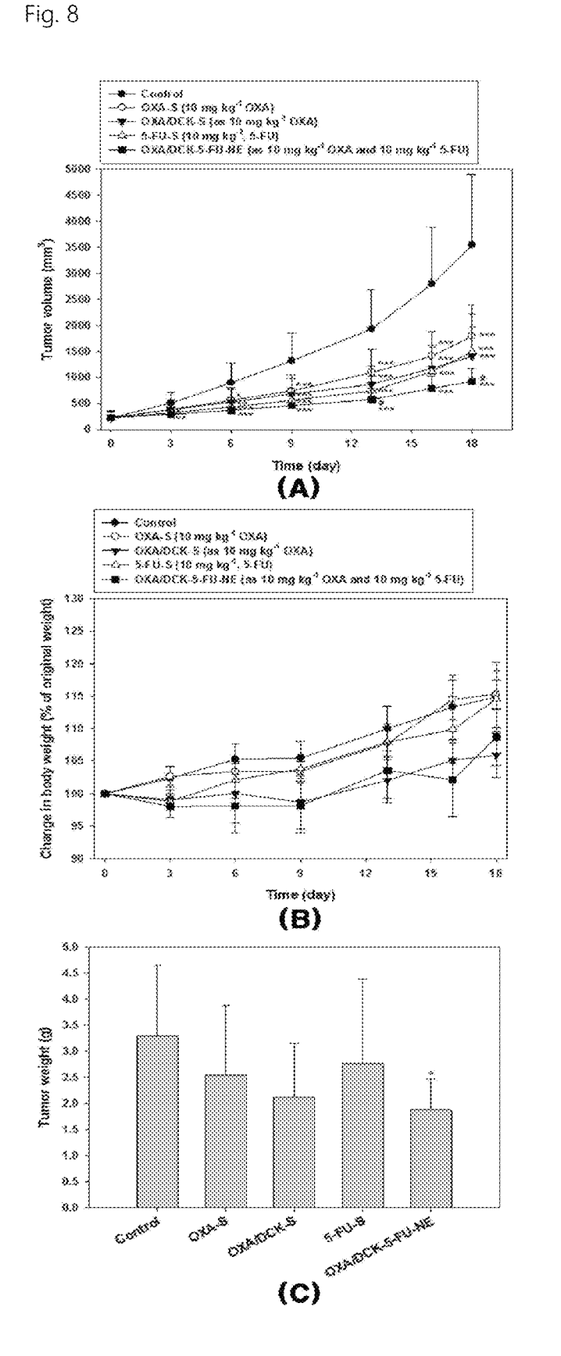
FIG. 8 shows, according to Example 11 of the present invention, (A) The size of the tumor tissue over time,
(B) Mouse weight changes over time,
(C) Weight of the extracted tumor tissue after 18 days of administration.

As shown in FIG. 8(A), After a daily oral administration of OXA/DCK-S in mice transplanted with tumor cells, the growth of tumor tissues was inhibited by 60.3% and 21.4% compared to the control and OXA-S group, respectively.

5-FU-S solution group also delayed the growth of tumor tissue by 57.9% compared to the control group. Also, tumor growth in the group administered orally with the 5-FU aqueous solution did not show a significant difference in the effect of inhibiting tumor growth compared with the group administered orally with the OXA/DCK aqueous solution. In contrast, OXA/DCK-5FU-NE group maximally inhibited the increase in tumor volume compared to the control (73.9%), OXA-S (48.5%), OXA/DCK-S (34.4%), and 5-FU-S (38.1%) groups.

After 18 days of drug administration, tumor weights from the OXA/DCK-5FU-NE group also decreased by 43.0%, 26.0%, 11.6%, and 32.0% compared to the control, OXA-S, OXA/DCK-S, and 5-FU-S, respectively, but mice had no significant effect on body weight (FIGS. 8(B) and (C)).

Referring to FIG. 9, the sustained OXA/DCK-5-FU-NE group not only significantly reduced the proliferating cell density but also increased tumor apoptosis compared to the control group, OXA-S, OXA/DCK-S and 5-FU-S. These results may be due to the improvement of oral bioavailability of nanoemulsion comprising OXA/DCK ion-pairing complex and 5-FU and the synergistic effects of these drugs on tumor growth inhibition.

The present invention has been described above by way of example, and those skilled in the art will appreciate that various modifications may be made without departing from the essential characteristics of the present invention. Accordingly, the embodiments disclosed herein are not intended to limit the present invention but to describe the present invention, and the spirit and scope of the present invention are not limited by these embodiments. The protection scope of the present invention should be interpreted by the following claims, and all the technologies within the equivalent scope should be interpreted as being included in the scope of the present invention.

What is claimed is:

1. A method of preparing an oral delivery composition comprising oxaliplatin, comprising:
    (a) adding a positively charged bile acid derivative to oxaliplatin to form an ion-pairing complex;
    (b) adding a mixture of a primary surfactant and a primary co-surfactant to a primary oil phase;
    (c) mixing the ion-pairing complex with the mixture resulting from step (b) to obtain a water-in-oil (w/o) primary nanoemulsion;
    (d) adding a mixture of a secondary surfactant and a secondary co-surfactant to the w/o primary nanoemulsion to obtain a water-in-oil-in-water (w/o/w) secondary nanoemulsion.

2. The method according to claim 1, wherein the bile acid derivative is $N^\alpha$-deoxycholyl-L-lysyl-methylester (DCK).

3. The method according to claim 1, wherein the primary oil phase is any one or more selected from the group consisting of silicone oil, ester oil, hydrocarbon oil, propylene glycol monocaprylate, propylene glycol dicaprolate/dicaprate, oleoyl polyoxyl-6 glycerides, lauroyl polyoxyl-6 glycerides, linoleoyl polyoxyl-6 glycerides, medium chain triglycerides, oleic acid, stearic acid, glyceryl dibehenate, glycerol monostearate, and castor oil.

4. The method according to claim 1, wherein the primary and secondary surfactants are each independently any one or more selected from the group consisting of poloxamer, caprylocaproyl polyoxyl-8 glycerides, Cremophor, caprylic/capric mono- and diglycerides, lauroyl polyoxyl-32 glycerides, solutrol, polysorbate, and sorbitan Monolaurate.

5. The method according to claim 1, wherein the primary and secondary surfactants are each independently one or more selected from the group consisting of diethylene glycol monoethyl ether, polysorbate, polyethylene glycol, butylene glycol, propylene glycol, ethanol, and isopropanol.

6. The method according to claim 1, wherein the bile acid derivative is added in an amount of 0.5 to 5 moles per 1 mole of oxaliplatin.

7. The method according to claim 1, wherein the w/o primary nanoemulsion (oil phase) in the w/o/w secondary nanoemulsion is included in an amount of 1 to 40% by weight, based on the total weight of the composition.

8. The method according to claim 1, wherein the mixture of the primary surfactant and the primary co-surfactant and the mixture of the secondary surfactant and the secondary co-surfactant are included in an amount of 5 to 90% by weight, based on the total weight of the composition.

9. The method according to claim 1, wherein the primary and secondary co-surfactants are mixed each independently in a weight ratio of 1:0.1 to 1:10 with respect to the primary and secondary surfactants.

10. The method according to claim 1, further comprising in step (a) adding an anti-aggregation agent selected from the group consisting of monosaccharides, polysaccharides, dietary fibers, gums and proteins.

11. The method according to claim 10, wherein the anti-aggregation agent is added in an amount of 0.1 to 100 parts by weight, based on 1 part by weight of oxaliplatin.

12. The method according to claim 1, wherein the w/o primary nanoemulsion comprises in the inner aqueous phase a hydrophilic active ingredient selected from the group consisting of 5-fluorouracil (5-FU) and leucovorin.

13. The method according to claim 1, wherein the w/o/w secondary nanoemulsion comprises an oil-soluble active ingredient in the oil phase, selected from the group consisting of an poorly soluble anticancer agent, curcumin, quercetin, natural extract containing curcumin or quercetin as an active ingredient and a mixture thereof.

14. An oral delivery composition comprising oxaliplatin prepared by the method according to claim 1.

* * * * *